US011220734B2

(12) United States Patent
Chen et al.

(10) Patent No.: US 11,220,734 B2
(45) Date of Patent: Jan. 11, 2022

(54) MAGNESIUM-BASED BULK METALLIC GLASS COMPOSITE AND SUTURE ANCHOR THEREOF

(71) Applicants: National Central University, Taoyuan (TW); Taipei Medical University, Taipei (TW)

(72) Inventors: Chih-Hwa Chen, Taipei (TW); Shian-Ching Jang, Taoyuan (TW); Hsiang-Ho Chen, Taipei (TW); Lau-Yuen Woo, Taipei (TW); Erh-Yuan Chuang, Taipei (TW)

(73) Assignees: NATIONAL CENTRAL UNIVERSITY, Taoyuan (TW); TAIPEI MEDICAL UNIVERSITY, Taipei (TW)

( * ) Notice: Subject to any disclaimer, the term of this patent is extended or adjusted under 35 U.S.C. 154(b) by 236 days.

(21) Appl. No.: 16/412,496

(22) Filed: May 15, 2019

(65) Prior Publication Data
US 2019/0352757 A1 Nov. 21, 2019

Related U.S. Application Data

(60) Provisional application No. 62/671,449, filed on May 15, 2018.

(51) Int. Cl.
C22C 45/00 (2006.01)
C22C 1/00 (2006.01)
A61L 31/12 (2006.01)
C22C 23/04 (2006.01)

(52) U.S. Cl.
CPC .......... *C22C 45/005* (2013.01); *A61L 31/124* (2013.01); *C22C 1/002* (2013.01); *C22C 23/04* (2013.01); *C22C 2200/02* (2013.01)

(58) Field of Classification Search
None
See application file for complete search history.

(56) References Cited

U.S. PATENT DOCUMENTS

| | | | | |
|---|---|---|---|---|
| 2002/0003013 A1* | 1/2002 | Hays | ....................... | C22C 45/00 148/561 |
| 2012/0197296 A1* | 8/2012 | Mayer | ................ | A61B 17/0401 606/232 |
| 2014/0248288 A1* | 9/2014 | Kumta | .................... | A61L 27/58 424/172.1 |
| 2015/0127048 A1* | 5/2015 | Curtis | ................ | A61B 17/0401 606/232 |

FOREIGN PATENT DOCUMENTS

CN 103602930 A * 2/2014

OTHER PUBLICATIONS

English Translation of CN 103602930 (originally published Feb. 26, 2014) from Espacenet.*
Gu, X. et al., "Mg—Ca—Zn bulk metallic glasses with high strength and significant ductility", J. of Materials Research, vol. 20, No. 8, pp. 1935-1938, Aug. 2005.*
Guosong Wu et al., "Surface design of biodegradable magnesium alloys", Surface & Coatings Technology, 233 (2013) 2-12.

* cited by examiner

Primary Examiner — George Wyszomierski
(74) Attorney, Agent, or Firm — Bacon & Thomas, PLLC

(57) ABSTRACT

A magnesium-based bulk metallic glass composite includes a magnesium-based bulk metallic glass composite comprising a magnesium-based material and a TiZr alloy.

15 Claims, 7 Drawing Sheets

MAGNESIUM-BASED BULK METALLIC GLASS COMPOSITE AND SUTURE ANCHOR THEREOF

CROSS REFERENCE TO RELATED APPLICATION

This application claims the benefit of filing date of U.S. Provisional Application Ser. No. 62/671,449, entitled "Studies on biodegradable Mg-based metallic glass for developing a new suture anchor useful in sports medicine" filed May 15, 2018 under 35 USC § 119(e)(1).

BACKGROUND OF THE INVENTION

1. Field of the Invention

The present invention relates to a magnesium-based bulk metallic glass composite and a suture anchor thereof and, more particularly, to a magnesium-based bulk metallic glass composite comprising a TiZr alloy.

2. Description of Related Art

At present, a suture anchor is one of the most common fixation devices for fixing tendons and ligaments to bones. According to the material type, suture anchors are categorized into metal suture anchor and non-metallic suture anchor. Among them, the metallic material of the suture anchor are stainless steel (316L) or titanium alloy (Ti6Al4V) mainly, and these metallic suture anchor have good mechanical properties. However, since the Young's Modulus of such metallic suture anchors mismatch that of bone, it causes stress shielding effect, and thus results in osteolysis, reducing the stability of the implant. In addition, the implant for fixation still stays in the body after the bone is healed, leading to a potential risk of releasing metallic ion. Therefore, a secondary surgery is required for removing the implant and it brings extra pain to the patient.

Although a biodegradable suture anchor, such as a polymer suture anchor including polylactic acid (PLA), can avoid the release of metallic ions, the polymer suture anchor has disadvantages including low Young's Modulus, poor mechanical properties such as brittleness and release of acid substances after degradation causing inflammation in the peripheral tissues.

Therefore, it is desirable to provide an improved suture anchor to mitigate or obviate the aforementioned problems.

SUMMARY OF THE INVENTION

One object of the present invention is to provide a magnesium-based bulk metallic glass composite (BMGC), comprising a magnesium-based material and a TiZr alloy.

In the magnesium-based bulk metallic glass composite according to one aspect of the present invention, the TiZr alloy preferably is a $Ti_aZr_wTa_bSi_xSn_yCo_z$ alloy, wherein a is 40-44, b is 1-5, and the sum of w, x, y, z is 55.

In the magnesium-based bulk metallic glass composite according to one aspect of the present invention, the magnesium-based material may be a Mg—Zn—Ca material. Preferably, the Mg—Zn—Ca material is a $Mg_aZn_bCa_c$ material, wherein 65≤a≤70, 25≤b≤30, and 3≤c≤7. More preferably, the Mg—Zn—Ca material is a $Mg_{66}Zn_{29}Ca_5$ material.

In the magnesium-based bulk metallic glass composite according to one aspect of the present invention, a volume fraction of the TiZr alloy may be in a range from 1 vol. % to 30 vol. %, based on a total volume of the magnesium-based bulk metallic glass composite. Preferably, the volume fraction of the TiZr alloy is 5 vol. %, 10 vol. %, 15 vol. %, 20 vol. % or 30 vol. %, based on a total volume of the magnesium-based bulk metallic glass composite.

In the magnesium-based bulk metallic glass composite according to one aspect of the present invention, a particle size of the TiZr alloy may be in a range from 25 µm to 45 µm.

In the magnesium-based bulk metallic glass composite according to one aspect of the present invention, the magnesium-based bulk metallic glass composite may be amorphous.

Another object of the present invention is to provide a suture anchor, comprising: an anchor body having a proximal end and a distal end, wherein a thread having a plurality of turns is disposed on an outer surface of the anchor body, a transverse eyelet is disposed near the distal end, and a plurality of suture channels are disposed on the outer surface of the anchor body; wherein the suture anchor is made of a magnesium-based bulk metallic glass composite comprising a magnesium-based material and a TiZr alloy.

In the suture anchor according to one aspect of the present invention, the TiZr alloy preferably is a $Ti_aZr_wTa_bSi_xSn_yCo_z$ alloy, wherein a is 40-44, b is 1-5, and the sum of w, x, y, z is 55.

In the suture anchor according to one aspect of the present invention, the magnesium-based material may be a Mg—Zn—Ca material. Preferably, the Mg—Zn—Ca material is a $Mg_aZn_bCa_c$ material, wherein 65≤a≤70, 25≤b≤30, and 3≤c≤7. More preferably, the magnesium-based material is a $Mg_{66}Zn_{29}Ca_5$ material.

In the suture anchor according to one aspect of the present invention, a volume fraction of the TiZr alloy may be in a range from 1 vol. % to 30 vol. %, based on a total volume of the magnesium-based bulk metallic glass composite. Preferably, the volume fraction of the TiZr alloy may be 5 vol. %, 10 vol. %, 15 vol. %, 20 vol. %, or 30 vol. % based on a total volume of the magnesium-based bulk metallic glass composite.

In the suture anchor according to one aspect of the present invention, a particle size of the TiZr alloy may be in a range from 25 µm to 45 µm.

In the suture anchor according to one aspect of the present invention, the magnesium-based bulk metallic glass composite may be amorphous.

Yet another object of the present invention is to provide a method for preparing a magnesium-based bulk metallic glass composite, comprising steps of: (a) providing a Mg—Zn—Ca raw material and TiZr alloy; (b) induction melting a mixture of the Mg—Zn—Ca raw material and the TiZr alloy to form a melt; (c) cooling down the melt to form a Mg—Zn—Ca master alloy composite ingot; (d) remelting the Mg—Zn—Ca master alloy composite ingot; and (e) injecting the remelted Mg—Zn—Ca alloy composite melt into a mold to form a magnesium-based bulk metallic glass composite.

In the method for preparing a magnesium-based bulk metallic glass composite according to one aspect of the present invention, the TiZr alloy preferably is a $Ti_aZr_wTa_bSi_xSn_yCo_z$ alloy, wherein a is 40-44, b is 1-5, and the sum of w, x, y, z is 55.

In the method for preparing a magnesium-based bulk metallic glass composite according to one aspect of the present invention, the Mg—Zn—Ca raw material preferably is a $Mg_aZn_bCa_c$ raw material, wherein 65≤a≤70, 25≤b≤30, and 3≤c≤7. More preferably, the Mg—Zn—Ca raw material is a $Mg_{66}Zn_{29}Ca_5$ raw material.

In the method for preparing a magnesium-based bulk metallic glass composite according to one aspect of the present invention, a volume fraction of the TiZr alloy may be in a range from 1 vol. % to 30 vol. %, based on a total volume of the magnesium-based bulk metallic glass composite. Preferably, the TiZr alloy may be 5 vol. %, 10 vol. %, 15 vol. % 20 vol. %, or 30 vol. % based on a total volume of the magnesium-based bulk metallic glass composite.

In the method for preparing a magnesium-based bulk metallic glass composite according to one aspect of the present invention, a particle size of the TiZr alloy may be in a range from 25 μm to 45 μm.

In the method for preparing a magnesium-based bulk metallic glass composite according to one aspect of the present invention, the step (b) may be carried out by a high-frequency induction furnace.

Further object of the present invention is to provide a method for preparing a suture anchor, comprising steps of: (a) providing a Mg—Zn—Ca raw material and TiZr alloy; (b) induction melting a mixture of the Mg—Zn—Ca raw material and the TiZr alloy to form a melt; (c) cooling down the melt to form a Mg—Zn—Ca master alloy composite ingot; (d) remelting the Mg—Zn—Ca master alloy composite ingot; and (e) injecting the remelted Mg—Zn—Ca alloy composite melt into a mold having a suture anchor shape to form the suture anchor made from a magnesium-based bulk metallic glass composite.

In the method for preparing a suture anchor according to one aspect of the present invention, the TiZr alloy preferably is a $Ti_aZr_wTa_bSi_xSn_yCo_z$ alloy, wherein a is 40-44, b is 1-5, and the sum of w, x, y, z is 55.

In the method for preparing a suture anchor according to one aspect of the present invention, the Mg—Zn—Ca raw material preferably is a $Mg_aZn_bCa_c$ raw material, wherein 65≤a≤70, 25≤b≤30, and 3≤c≤7. More preferably, the Mg—Zn—Ca raw material is a $Mg_{66}Zn_{29}Ca_5$ raw material.

In the method for preparing a suture anchor according to one aspect of the present invention, a volume fraction of the TiZr alloy may be in a range from 1 vol. % to 30 vol. %, based on a total volume of the magnesium-based bulk metallic glass composite. Preferably, the volume fraction of the TiZr alloy may be 5 vol. %, 10 vol. %, 15 vol. %, 20 vol. %, or 30 vol. % based on a total volume of the magnesium-based bulk metallic glass composite.

In the method for preparing a suture anchor according to one aspect of the present invention, a particle size of the TiZr alloy may be in a range from 25 μm to 45 μm.

In the method for preparing a suture anchor according to one aspect of the present invention, the magnesium-based bulk metallic glass composite may be amorphous.

In the method for preparing a suture anchor according to one aspect of the present invention, the step (b) may be carried out by a high-frequency induction furnace.

Other objects, advantages, and novel features of the invention will become more apparent from the following detailed description when taken in conjunction with the accompanying drawings.

DETAILED DESCRIPTION OF THE PREFERRED EMBODIMENT

PREPARATION EXAMPLE 1

To obtain Mg-based bulk metallic glass composites (BMGCs) comprising different volume fractions of TiZr alloy (Vf=5, 10, 15, 20, and 30 vol. %), an induction melting process under an argon atmosphere was carried out.

Firstly, Mg, Zn, Ca (>99.9% purity) were provided and then the Ti—Zr—Ta—Si—Sn—Co alloy particle (particle size: 25-45 μm) was added, the mixture was melted by induction melting under the argon atmosphere. Then the melt was churned mechanically until the melt was homogeneous and then cooled down rapidly so as to obtain a $Mg_{66}Zn_{29}Ca_5$—TiZr composite ingot having the homogeneous mixture, wherein the $Mg_{66}Zn_{29}Ca_5$—TiZr composite ingot is amorphous.

Afterward, the $Mg_{66}Zn_{29}Ca_5$—TiZr composite ingot was placed in a quartz tube for remelting and then injected, by argon pressure, into a water-cooled Cu mold to form a Mg-based BMGC rod having a length of 20 mm and a diameter of 2 mm. The Mg-based BMGC rod was then cut into 4 mm in length thereby forming a Mg-based BMGC rod having a length of 4 mm and a diameter of 2 mm. The Mg-based BMGC rod was polished for both ends, and the specimens of $Mg_{66}Zn_{29}Ca_5$ BMGC with 5 vol. %, 10 vol. %, 15 vol. %, 20 vol. %, and 30 vol. % TiZr alloy were obtained, respectively.

PREPARATION EXAMPLE 2

Figure 1:
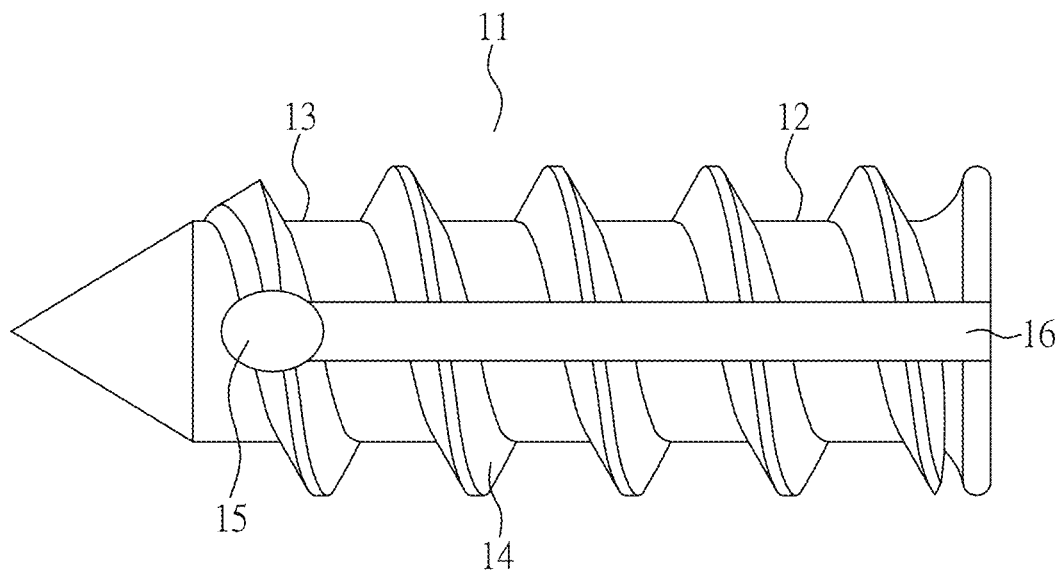
FIG. 1 shows a side view of a suture anchor according to one embodiment of the present invention.
Figure 2:
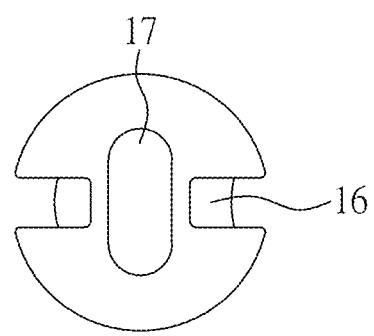
FIG. 2 shows a top view of a suture anchor according to one embodiment of the present invention.

FIG. 1 shows a side view of a suture anchor of the present invention; FIG. 2 shows a top view of a suture anchor of the present invention.

FIG. 1 and FIG. 2 show a preferred embodiment of the suture anchor of the present invention, comprising an anchor body 11 having a proximal end 12 and a distal end 13, wherein a thread 14 having a plurality of turns is disposed on an outer surface of the anchor body 11, a transverse eyelet 15 is disposed near the distal end 13, and a plurality of suture channels 16 are disposed on the outer surface of the anchor body 11. In addition, a drive channel 17 is provided within the anchor body 11 along the longitudinal axis of the anchor body 11. Preferably, the suture anchor is prepared by the following preparation method.

To obtain a suture anchor made from Mg-based bulk metallic glass composites (BMGCs) comprising 15 vol. % TiZr alloy, an induction melting process under an argon atmosphere was conducted.

Firstly, Mg, Zn, Ca (>99.9% purity) were provided and then Ti—Zr—Ta—Si—Sn—Co particles (particle size: 25-45 μm) were added, the mixture was melted by induction melting under the argon atmosphere. Then the melt was churned mechanically until the melt was homogeneous and then cooled down rapidly so as to obtain a $Mg_{66}Zn_{29}Ca_5$—TiZr composite ingot having the homogeneous mixture, wherein the $Mg_{66}Zn_{29}Ca_5$—TiZr composite ingot was amorphous.

Afterward, the $Mg_{66}Zn_{29}Ca_5$—TiZr composite ingot was placed in a quartz tube for remelting and then injected, by argon pressure, into a water-cooled Cu mold to form a Mg-based BMGC anchor having a length of 16.5 mm and a diameter of 6.5 mm.

TEST EXAMPLE 1

X-ray Diffraction and Optical Microscope

Figure 3:
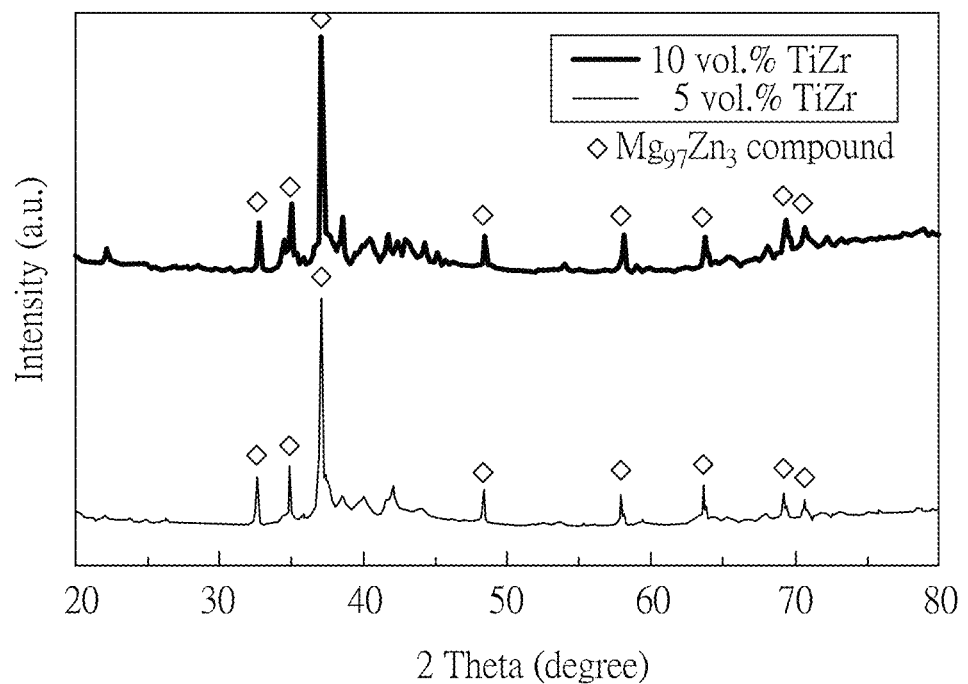
FIG. 3 shows X-ray diffraction (XRD) pattern of the $Mg_{66}Zn_{29}Ca_5$ BMGCs comprising 5 vol. % and 10 vol. % TiZr alloy according to one embodiment of the present invention.
Figure 4B:
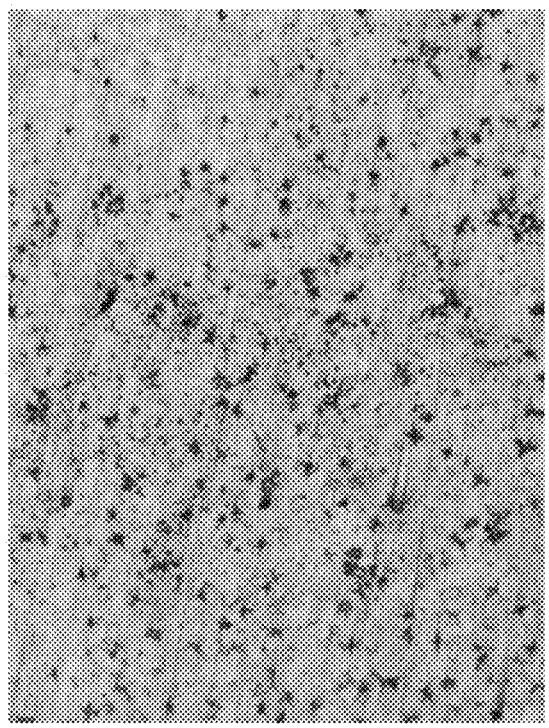
FIGS. 4A and 4B respectively show optical microscope (OM) images of the $Mg_{66}Zn_{29}Ca_5$ BMGCs comprising 5 vol. % and 10 vol. % TiZr alloy according to one embodiment of the present invention.
Figure 4A:
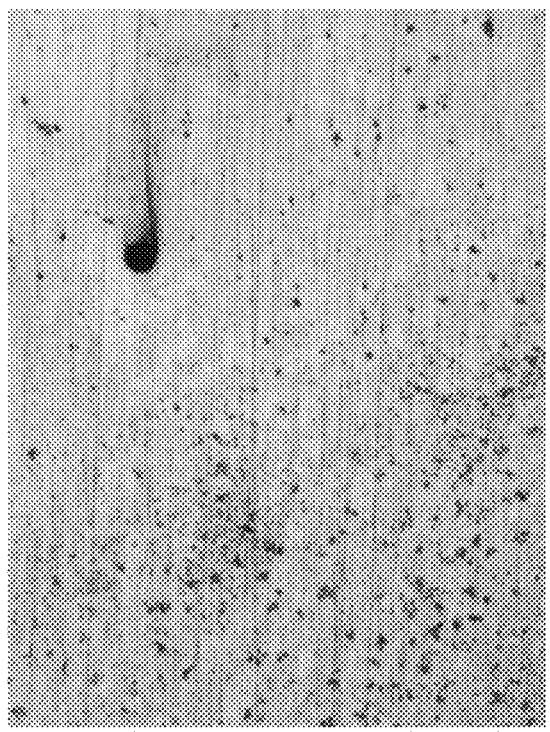

FIG. 3 shows X-ray diffraction (XRD) pattern of the $Mg_{66}Zn_{29}Ca_5$ BMGCs with TiZr alloy. FIGS. 4A and 4B show optical microscope (OM) images of the $Mg_{66}Zn_{29}Ca_5$ BMGCs with 5 vol. % and 10 vol. % TiZr alloy, respectively.

The amorphous state of the specimen obtained from Preparation Example 1 was examined by X-ray diffraction (XRD, Shimadzu XRD6000, Shimadzu Corporation, Kyoto, Japan) with mono chromatic Cu-Kα radiation.

TEST EXAMPLE 2

Fracture Toughness

Fracture toughness tests for the specimens of $Mg_{66}Zn_{29}Ca_5$ BMGC comprising 5%, 10%, and 15% TiZr alloy obtained from Preparation Example 1 were conducted via the indentation method. The test results were shown in Table 1.

TABLE 1

|  | MgZnCa BMG | 5 vol. % TiZr | 10 vol. % TiZr | 15 vol. % TiZr |
|---|---|---|---|---|
| Fracture toughness (MPa · m^½) | 1.98 | 6.50 | 5.29 | 12.26 |
| Standard deviation | — | — | 0.35 | 3.97 |

As shown in Table 1, the $Mg_{66}Zn_{29}Ca_5$ BMGC rods comprising 5%, 10%, and 15% TiZr alloy significantly enhanced the fracture toughness. It was obvious that the addition of TiZr alloy effectively enhanced the fracture toughness.

TEST EXAMPLE 3

Mechanical Evaluation

Mechanical evaluation of the suture anchor obtained from Preparation Example 2 was conducted following an industry-standard testing method using a rigid PU foam (Sawbone, GP 20) in order to determine the maximum push out force of the suture anchor disclosed by the present invention. Compared to a commercially available titanium suture anchor SUPER REVO®FT (ConMed) and polymer suture anchor GENESYS® CROSS FT of similar dimensions (6.5 mm diameter by 16.5 mm length), the suture anchors from Preparation Example 2 of the present invention exhibited higher push out strength than that of other commercial products, as shown in Table 2.

TABLE 2

| | Push out strength (N) | | | | | | |
|---|---|---|---|---|---|---|---|
| | n | | | | | | |
| Suture anchor | 1 | 2 | 3 | 4 | 5 | 6 | mean ± SD |
| Preparation Example 2 | 925.84 | 950.24 | 998.09 | 881.29 | 968.43 | 893.42 | 936.05 ± 41.04 |
| SUPER REVO ®FT | 544.07 | 576.63 | 620.81 | 639.73 | 594.15 | 601.17 | 596.09 ± 30.63 |
| GENESYS ® CROSS FT | 457.64 | 327.60 | 399.74 | | | | 394.99 ± 53.19 |

TEST EXAMPLE 4

Cell Cytotoxicity

Figure 5:
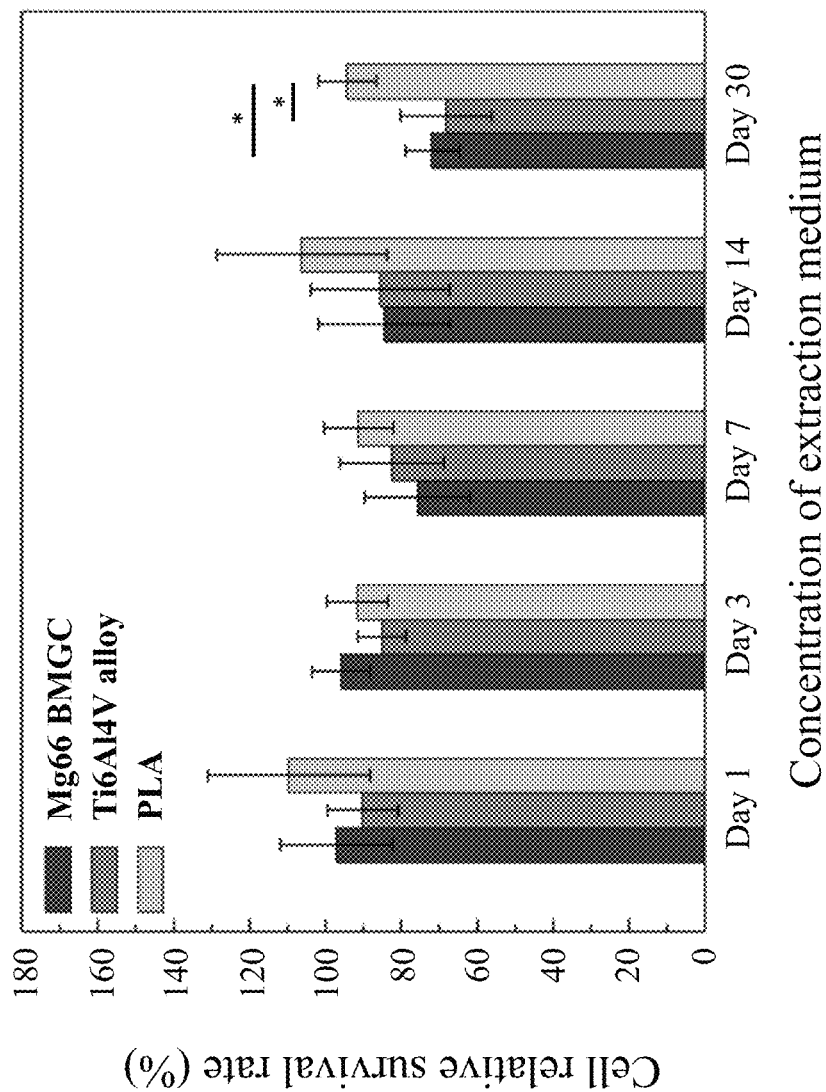
FIG. 5 shows cell relative survival rate in the different medium where a suture anchor of $Mg_{66}$ BMGC ($Mg_{66}Zn_{29}Ca_5$ BMGC), Ti6Al4V alloy, or polylactic acid (PLA) is immersed according to one embodiment of the present invention.

FIG. 5 shows cell relative survival rate in the different medium where a suture anchor of $Mg_{66}$ BMGC ($Mg_{66}Zn_{29}Ca_5$ BMGC), Ti6Al4V alloy, or polylactic acid (PLA) was immersed.

Rabbit primary osteoblasts from the pelvic bone were provided for the biocompatibility test, and the biocompatibility test was conducted by means of indirect contact method. In the present embodiment, the Mg-based BMGC suture anchor obtained from Preparation Example 2 was immersed in the DMEM, and the precipitate medium was collected for different period of time (1, 3, 7, 14, and 30 days). The rabbit primary osteoblasts were seeded into a 96-well culture plate (5000 cells/well), and the medium containing Dulbecco's modified Eagle medium (DMEM) and 10% fetal bovine serum was removed after 24 hours. Then the precipitate medium was added to the 96-well culture plate and the plate was then placed in an incubator at 37° C. in 5% $CO_2$ for 24 hours. Afterward, 10 ml of 3-(4,5-dimethylthiazol-2-yl)-2,5-diphenyltetrazolium bromide solution was then added to each well of the plate, and the plate was placed in the incubator at 37° C. in 5% $CO_2$ for 2 hours. Then, 100 ml of dimethyl sulfoxide (DMSO) was added, followed by measuring the optical density (OD) at 560 nm using an enzyme-linked immuno-sorbent assay (ELISA) reader.

As shown in FIG. 5, the cell viability of $Mg_{66}Zn_{29}Ca_5$ BMGC suture anchor was higher than that of Ti6Al4V alloy in the medium where the suture anchor had been immersed for 30 days. It suggested that the suture anchor of Ti6Al4V alloy was more prone to release metallic ions within 30 days, causing higher cytotoxicity for the cells. Therefore, the suture anchor of the present invention had good biocompatibility.

TEST EXAMPLE 5

Migration Test

Figure 6A:
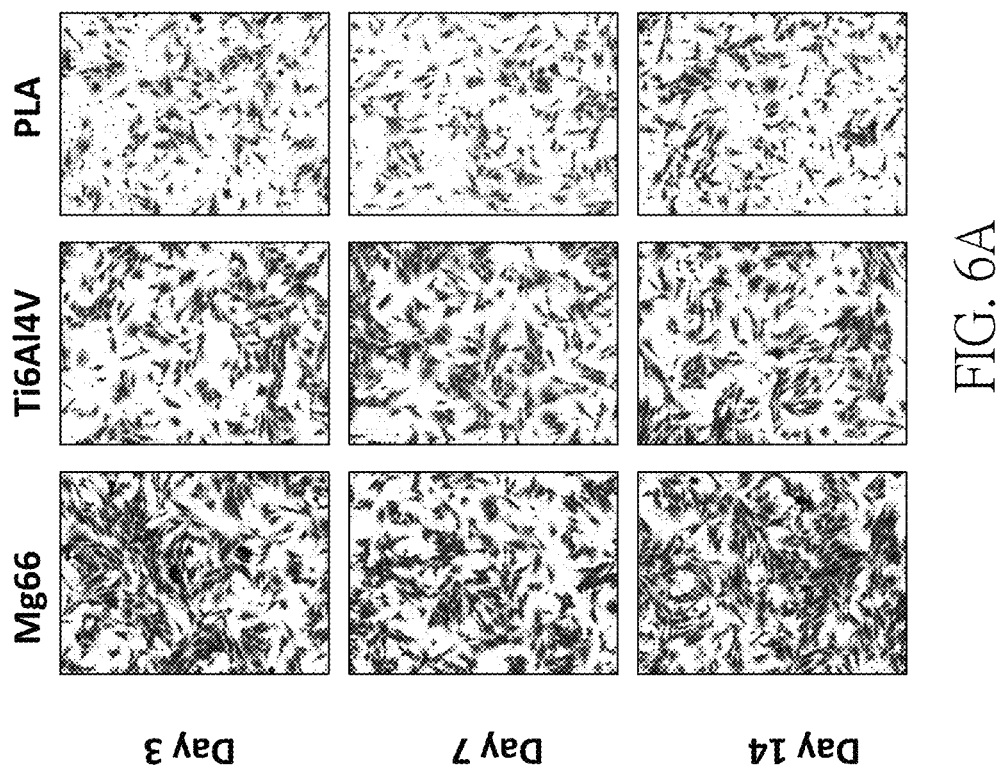
FIG. 6A shows cell migration images of the suture anchor according to one embodiment of the present invention.
Figure 6B:
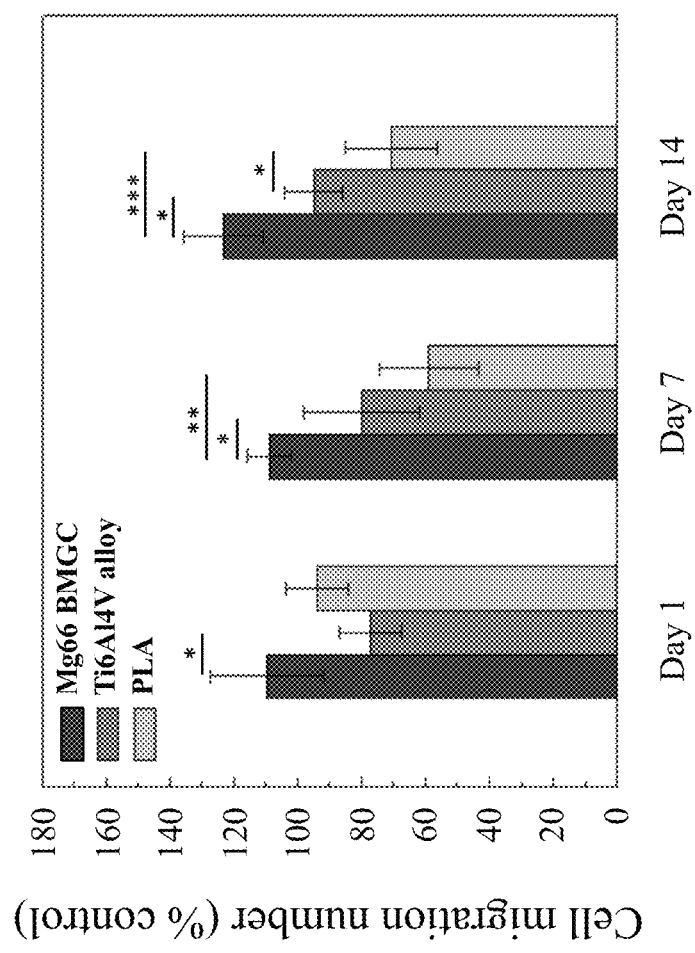
FIG. 6B shows a quantification diagram of the FIG. 6A.

FIG. 6A shows cell migration images of the suture anchor of the present invention; FIG. 6B shows a quantification diagram of the FIG. 6A.

The in vitro migration capacity of rabbit primary osteoblasts was assessed by transmembrane assay using 8 μm pore size inserts. The migration capacity of the rabbit primary osteoblasts was stimulated several times (on days 3, 7, and 14) for the $Mg_{66}Zn_{29}Ca_5$ BMGC, Ti6Al4V alloy, and PLA precipitate media. First, cells were suspended in DMEM (Gibco®, Carlsbad, Calif., USA) with a density of $2.5 \times 10^4$ cells/mL per well and seeded with 200 μL in the inserts (one side of the membrane). Second, 750 μL of the precipitate medium was added to the opposite side (lower chamber) at varying times. After incubation at 37° C. for 12 h, the medium was removed from the inserts and the cells were gently washed twice in PBS. The cells were then treated with a fixative (4% formaldehyde) for two minutes at room temperature. Next, the fixative was removed, and the cells were washed twice with PBS before undergoing permeabilization with 100% methanol. After this, the cells were stained with crystal violet for 20 min at room temperature. The non-migrating cells were scraped off, and the migrated cells were captured and counted using an optical microscope (Primovert; Zeiss, Oberkochen, Germany) for comparison using automated Image J software.

It is noted that the ability of an implanted material to recruit cells from the surrounding tissue is important with respect to accelerating the healing process. For the bone healing process, the attraction of cells that surround the damaged or defective tissue does not only enhance the function of these cells, but also increases the number of cells and quickens the healing progress. As shown in FIG. 6A and FIG. 6B, $Mg_{66}$ BMGC ($Mg_{66}Zn_{29}Ca_5$ BMGC) had higher cell migration numbers compared to the commercial products (Ti6Al4V alloy and PLA). Therefore, the suture anchor of the present invention had better recruitment ability that was favorable for the bone healing process.

TEST EXAMPLE 6

Extracellular Calcium Deposition

Figure 7:
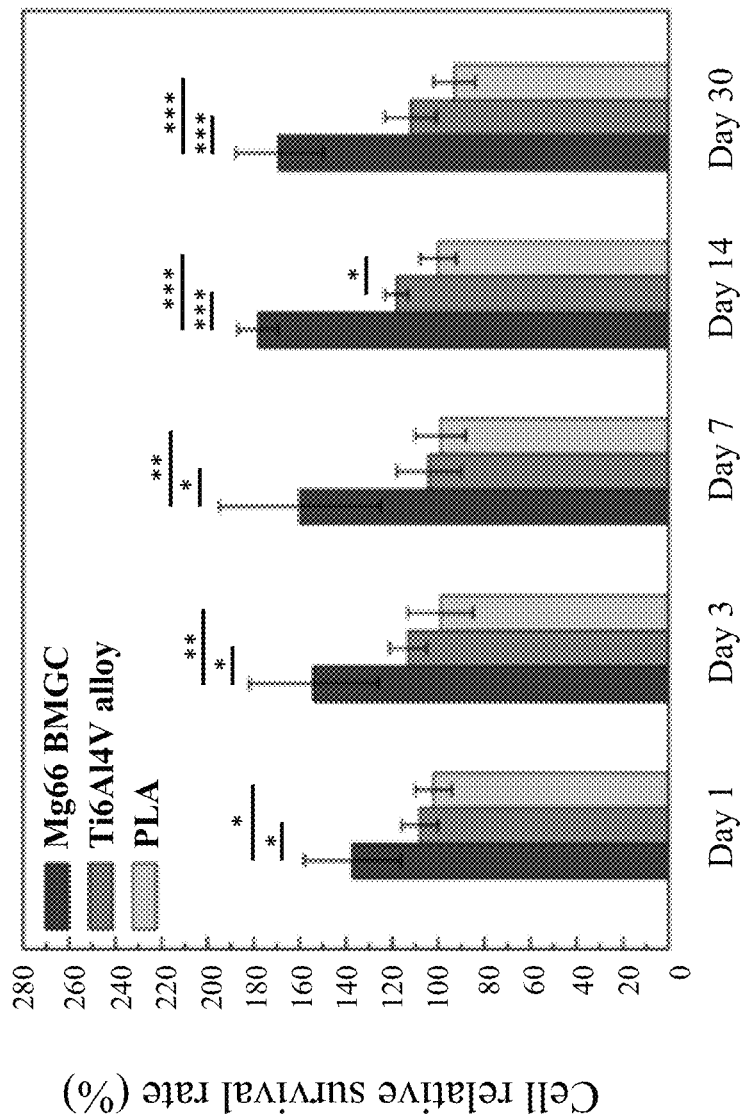
FIG. 7 shows a diagram of extracellular calcium deposition of a suture anchor according to one embodiment of the present invention.

FIG. 7 shows a diagram of extracellular calcium deposition of a suture anchor of the present invention.

Rabbit primary osteoblasts were used to evaluate the extracellular calcium deposited by the ions released from $Mg_{66}Zn_{29}Ca_5$ BMGC, the Ti6Al4V alloy, and PLA. The precipitate medium contained the ions of the three materials collected at different times (at days 1, 3, 7, 14, and 30). The cell suspension (500 μL, $1 \times 10^4$ cells/well) was dispensed into 24-well culture plates and pre-incubated for 24 h in an incubator at 37° C. and under a 5% $CO_2$ atmosphere. Next, 10 μL of the precipitate medium was added to each of the 24-well culture plates, and they were cultured in an incubator for 72 h. The culture medium was then removed from each well, and the cells were gently washed with PBS (Gibco®) before they were treated with a fixative (4% formaldehyde) for 15 minutes at room temperature. The fixative was then removed, and the cells were washed three times with DI water. Then the extracellular matrix calcium was evaluated through alizarin red s (ARS) staining Afterward, the ratio of the stained area to the entire area of the culture well was quantified using Image J software for each extracted medium. The stained area of each group was normalized with the control group (without the simulation of any extracted medium).

As shown in FIG. 7, $Mg_{66}$ BMGC ($Mg_{66}Zn_{29}Ca_5$ BMGC) had higher ratio of calcium deposition compared to the commercial products (Ti6Al4V alloy and PLA). Therefore, the suture anchor of the present invention was favorable for calcium deposition so that it promoted bone proliferation.

The commercial suture anchor SUPER REVO®FT (ConMed) tested in the embodiment is made from titanium, and is undegradable. Compared to the SUPER REVO®FT, the suture anchor of the present invention has low degrading rate which is adjustable depending on the composition of the magnesium-based bulk metallic glass composite. Furthermore, the suture anchor of the present invention has higher push out strength than that of commercial products (for example, SUPER REV®FT and GENESYS® CROSS FT) so that it has better stability in a subject's body.

In addition, compared to the suture anchors of SUPER REVO®FT and GENESYS® CROSS FT, the suture anchor of the present invention is more advantageous to deposit calcium thereon. It is also found that the suture anchor of the present invention increases cell migration compared to the suture anchors of SUPER REVO®FT and GENESYS® CROSS FT. Therefore, the suture anchor of the present invention enhances osseointegration and increases bone proliferation.

As a result, the suture anchor of the present invention improves fracture toughness and has excellent strength. Furthermore, it has better biocompatibility than that of the commercial products. It is noted that the conventional suture anchor either has low biocompatibility (for example, Ti6Al4V suture anchor) or poor mechanical properties (for example, PLA suture anchor), whereas the suture anchor of the present invention has not only good biocompatibility but also excellent mechanical properties.

Although the present invention has been explained in relation to its preferred embodiment, it is to be understood that many other possible modifications and variations can be made without departing from the spirit and scope of the invention as hereinafter claimed.

What is claimed is:

1. A magnesium-based bulk metallic glass composite, which is a single material including a magnesium-based material and a TiZr alloy, wherein a particle size of the TiZr alloy is in a range from 25 μm to 45 μm.

2. The magnesium-based bulk metallic glass composite according to claim 1, wherein the magnesium-based material is a Mg—Zn—Ca material.

3. The magnesium-based bulk metallic glass composite according to claim 2, wherein the Mg—Zn—Ca material is a Mg66Zn29Ca5 material.

4. The magnesium-based bulk metallic glass composite according to claim 1, wherein a volume fraction of the TiZr alloy is in a range from 1 vol. % to 30 vol. %, based on a total volume of the magnesium-based bulk metallic glass composite.

5. The magnesium-based bulk metallic glass composite according to claim 4, wherein the volume fraction of the TiZr alloy is 5 vol. %, 10 vol. %, 15 vol. %, 20 vol. %, or 30 vol. %, based on a total volume of the magnesium-based bulk metallic glass composite.

6. A suture anchor, comprising:
   an anchor body having a proximal end and a distal end, wherein a thread having a plurality of turns is disposed on an outer surface of the anchor body, a transverse eyelet is disposed near the distal end, and a plurality of suture channels are disposed on the outer surface of the anchor body;
   wherein the suture anchor is made from a magnesium-based bulk metallic glass composite which is a single material including a magnesium-based material and a TiZr alloy, and a particle size of the TiZr alloy is in a range from 25 μm to 45 μm.

7. The suture anchor according to claim 6, wherein the magnesium-based material is a Mg—Zn—Ca material.

8. The suture anchor according to claim 6, wherein the magnesium-based material is a Mg66Zn29Ca5 material.

9. The suture anchor according to claim 6, wherein a volume fraction of the TiZr alloy is in a range from 1 vol. % to 30 vol. %, based on a total volume of the magnesium-based bulk metallic glass composite.

10. The suture anchor according to claim 9, wherein the volume fraction of the TiZr alloy is 5 vol. %, 10 vol. %, 15 vol. %, 20 vol. %, or 30 vol. %, based on a total volume of the magnesium-based bulk metallic glass composite.

11. A method for preparing a magnesium-based bulk metallic glass composite, comprising steps of:
   (a) providing a Mg—Zn—Ca raw material and TiZr alloy;
   (b) induction melting a mixture of the Mg—Zn—Ca raw material and the TiZr alloy to form a melt;
   (c) cooling down the melt to form a Mg—Zn—Ca master alloy composite ingot;
   (d) remelting the Mg—Zn—Ca master alloy composite ingot; and
   (e) injecting the remelted Mg—Zn—Ca alloy composite melt into a mold to form a magnesium-based bulk metallic glass composite, wherein the magnesium-based bulk metallic glass composite is a single material including a Mg—Zn—Ca material and the TiZr alloy, and a particle size of the TiZr alloy is in a range from 25 μm to 45 μm.

12. The method according to claim 11, wherein the Mg—Zn—Ca raw material is a Mg66Zn29Ca35 raw material.

13. The method according to claim 11, wherein a volume fraction of the TiZr alloy is in a range from 1 vol. % to 30 vol. %, based on a total volume of the magnesium-based bulk metallic glass composite.

14. The method according to claim 13, wherein the volume fraction of the TiZr alloy is 5 vol. %, 10 vol. %, 15 vol. %, 20 vol. % or 30 vol. %, based on a total volume of the magnesium-based bulk metallic glass composite.

15. The method according to claim 11, wherein the step (b) is carried out by a high-frequency induction furnace.

\* \* \* \* \*